US008111894B2

(12) United States Patent
Van De Haar

(10) Patent No.: US 8,111,894 B2
(45) Date of Patent: Feb. 7, 2012

(54) COMPUTER TOMOGRAPHY (CT) C-ARM SYSTEM AND METHOD FOR EXAMINATION OF AN OBJECT

(75) Inventor: Peter George Van De Haar, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 445 days.

(21) Appl. No.: 12/514,460

(22) PCT Filed: Nov. 7, 2007

(86) PCT No.: PCT/IB2007/054522
§ 371 (c)(1),
(2), (4) Date: May 12, 2009

(87) PCT Pub. No.: WO2008/059400
PCT Pub. Date: May 22, 2008

(65) Prior Publication Data
US 2010/0061610 A1    Mar. 11, 2010

(30) Foreign Application Priority Data

Nov. 16, 2006   (EP) .................................... 06124208

(51) Int. Cl.
*G06K 9/00* (2006.01)
(52) U.S. Cl. ................ 382/131; 378/4; 378/21; 378/62; 382/298; 382/132; 382/264
(58) Field of Classification Search ............. 378/4, 98.7, 378/62, 21, 19, 14, 16; 382/128–132, 264, 382/298, 299, 300, 205
See application file for complete search history.

(56) References Cited

U.S. PATENT DOCUMENTS
6,266,388 B1    7/2001   Hsieh
(Continued)

FOREIGN PATENT DOCUMENTS
EP         0492896 A2    7/1992
(Continued)

OTHER PUBLICATIONS

Feldkamp et al: "Practical Cone-Beam Algorithm"; Journal of the Optical Society of America, vol. 1, No. 6, Jun. 1984, pp. 612-619.

(Continued)

*Primary Examiner* — Gregory J Toatley
*Assistant Examiner* — Iyabo S Alli

(57) ABSTRACT

A Computer Tomography (CT) C-arm system and method for examination of an object is provided. The Computer Tomography (CT) C-arm system for examination of an object of interest, the CT- C-arm system comprises an X-ray tube adapted for generating X-rays, an X-ray detection unit to acquire a set of CT slices, wherein the X-ray tube, and the X-ray detection unit are adapted to be rotatable on a C-arm around a common axis around the object under examination and a processing unit by which the following steps are executable: acquiring a first 3D data volume of the CT slices using first scan parameters; adjusting the first data volume to a second data volume (segmented volume) such that voxel values of the first data volume of at least one predefined range of Hounsfield (H) are set to an at least one predefined H-value; generating a forward projection of the second data volume using the first scan parameters; reconstructing the projection to a third data volume; generating a fourth data volume (artefact-only volume) by subtracting the third volume with the second volume; generating a fifth volume by adding the first volume with the fourth volume.

8 Claims, 5 Drawing Sheets

U.S. PATENT DOCUMENTS

| | | | |
|---|---|---|---|
| 6,379,041 B1 * | 4/2002 | Schuetz et al. | 378/62 |
| 2004/0041807 A1 | 3/2004 | Hornegger et al. | |
| 2006/0008046 A1 | 1/2006 | Ruhrnschoph | |
| 2006/0227928 A1 | 10/2006 | Timmer | |

FOREIGN PATENT DOCUMENTS

| | | |
|---|---|---|
| WO | 02086822 A1 | 10/2002 |
| WO | 2005078661 A1 | 8/2005 |
| WO | 2006056942 A1 | 6/2006 |

OTHER PUBLICATIONS

Parker, D.: "Optimal Short Scan Convolution Reconstruction for Fanbeam CT"; Med. Phys. 9 (2), Mar./Apr. 1982, pp. 254-257.

Taguchi et al: "Algorithm for Image Reconstruction in Multi-Slice Helical CT"; Med. Phys. 25 (4), Apr. 1998, pp. 550-561.

Van Steevendaal et al: "A Reconstruction Algorithm for Coherent Scatter Computed Tomography Based on Filtered Back-Projection"; Med. Phys. 30 (9), Sep. 2003, pp. 2465-2474.

* cited by examiner

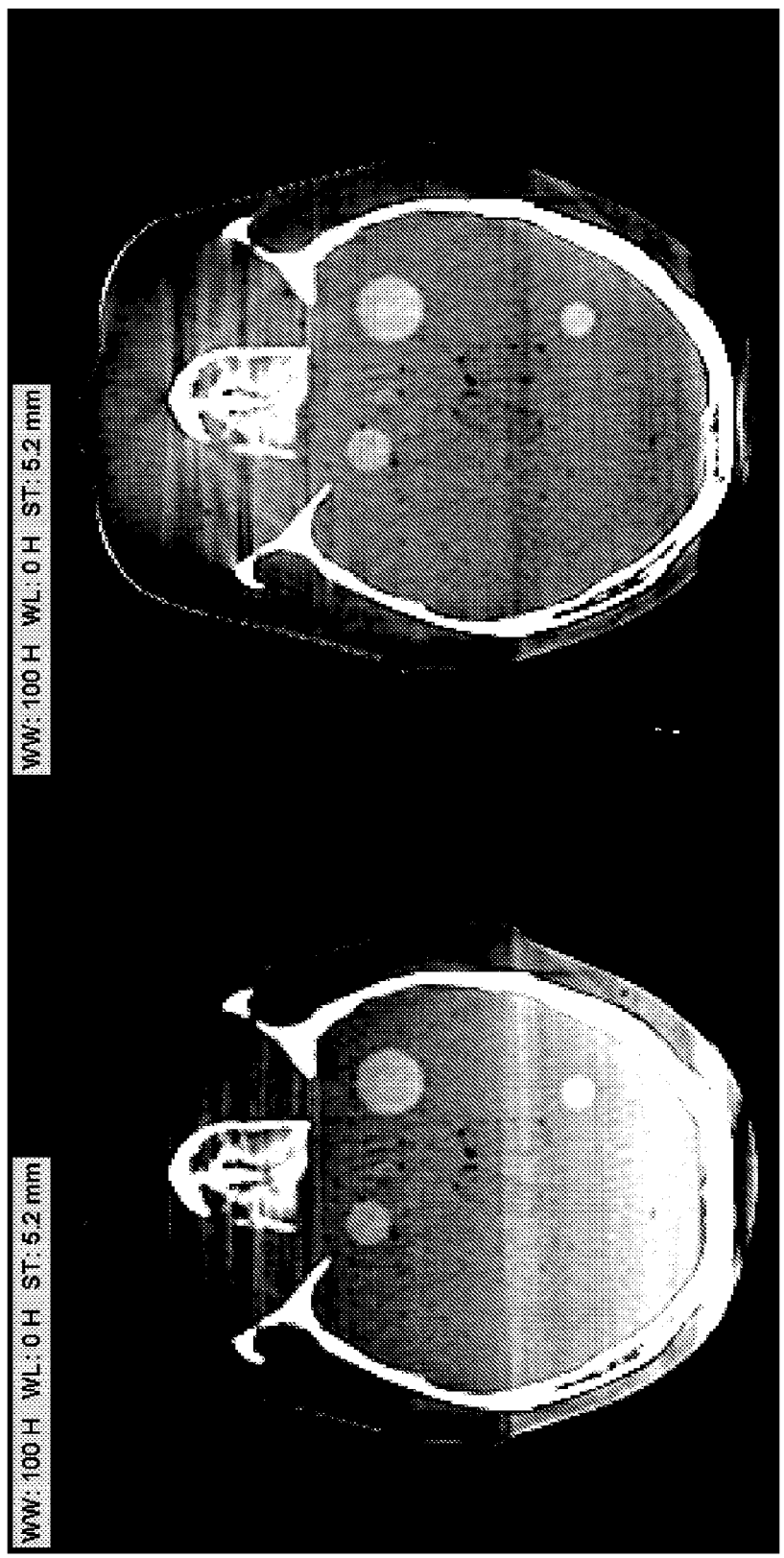

COMPUTER TOMOGRAPHY (CT) C-ARM SYSTEM AND METHOD FOR EXAMINATION OF AN OBJECT

FIELD OF INVENTION

The invention relates to a Computer Tomography (CT) C-arm system and a method for examination of an object. Further, the invention relates to a computer readable medium and a program element. More particular, the invention relates to a correction of 3D angular underscanning artefacts.

TECHNICAL BACKGROUND

Systems for producing an image of a physical object are widespread in several technical fields. One area of particular commercial interest is in the field of CT C-arm systems i.e. C-arm systems which are capable of CT-like 3D imaging. Good 3D image quality requires a C-arm rotation range of at least 180° plus fan angle.

In some medical or other cases it may be desirable to reduce the rotation range of the C-arm. One reason could be that the examination process is faster and therefore more economically. Also, a lower number of examined CT slices due to the reduced rotation range of the object causes less influences of X-rays to the object. Further, most C-arm systems have a limited angular range itself.

However, the image reconstruction of a CT-data volume of CT slices with an angular range of much less than 180° plus fan angle may cause an unacceptable level of strong artefacts due to the fact of strong density variations on material boundaries of the examined object of interest. More precisely, the reconstructed image may show artificial streaks or gradients.

SUMMARY OF THE INVENTION

Therefore, it would be desirable to provide an improved CT C-arm system and method for a better image quality.

Further, there may be a need to provide a system and a method for acquiring image data, which can be used in order to perform a scanning of an object under examination which scanning may be faster and/or more reliable than by known systems and which less image artefacts.

This need may be met by a system and a method for acquiring image data, a computer readable medium and a program element, according to the independent claims.

According to an embodiment of the invention a Computer Tomography (CT) C-arm system for examination of an object of interest is provided. The CT- C-arm system comprises an X-ray tube adapted for generating X-rays, an X-ray detection unit to acquire a set of CT slices, wherein the X-ray tube, and the X-ray detection unit are adapted to be rotatable on a C-arm around a common axis around the object under examination. A processing unit of the system acquires in a first step a first 3D data volume of the CT slices using first scan parameters. The first data volume may be a first-pass volume of the object of interest. In a second step the first data volume is adjusted to a second data volume (segmented volume) such that voxel values of the first data volume of at least one predefined range of Hounsfield (H) are set to an at least one predefined H-value. In a third step a forward projection of the second data volume using the first scan parameters of the first volume is generated. The aforesaid projection is reconstructed to a third data volume. By subtracting the third volume with the second volume a fourth data volume, a so-called artefact-only volume is generated by the processing unit. Finally, a fifth volume is generated by adding the first volume with the artefact-only volume.

Generally, the processor unit may uses suitable reconstruction algorithm as known from L. A. Feldkamp, L. C. Davis, and J. W. Kress, "*Practical cone-beam algorithms*", J. Opt. Soc. Am. A 6, pp. 612-619, 1984, from K. Taguchi, and H. Aradate, "*Algorithm for image reconstruction in multi-slice helical CT*", Med. Phys. 25, pp. 550-561, 1998 and from U.van Stevendaal, J.-P. Schlomka, A. Harding, and M. Grass, "*A reconstruction algorithm for coherent scatter computed tomography based on filtered back-projection*", Med. Phys. 30 (9), pp. 2465-2474, September 2003, for example.

It may be seen as the gist of an exemplary embodiment of the present invention that the pre-knowledge of anatomy is used by the invention in the case of angular underscanning Particularly the human anatomy consist of dense bone and water-like soft tissue, with strong density variations on the bone-tissue boundaries. To reduce the aforesaid artefacts a (further) pass is approached by an embodiment of the present invention: According to an exemplary embodiment of the present invention the first data volume is adjusted to the second data volume such that voxel values of the first data volume of a range between −500H and 200H are set to 0H. The artefacts caused by angular underscanning are further caused by bone-tissue boundaries, which can be identified and removed through the inventive pass or multi-pass approach.

According to an other exemplary embodiment of the present invention the first data volume is further adjusted to the second data volume such that voxel values of the first data volume less than −850H are set to −1000H.

These and other aspects of the present invention will become apparent from and elucidated with reference to the embodiment described hereinafter.

BRIEF DESCRIPTION OF THE DRAWINGS

An exemplary embodiment of the present invention will be described in the following, with reference to the following drawings.

FIG. 9A shows the same image as FIG. 3 for comparing with FIG. 9B

FIG. 9B shows the artefact corrected image as a result of an addition of the image data of FIG. 9A with the image data of FIG. 8.

DETAILED DESCRIPTION OF EXEMPLARY EMBODIMENT

Figure 1:
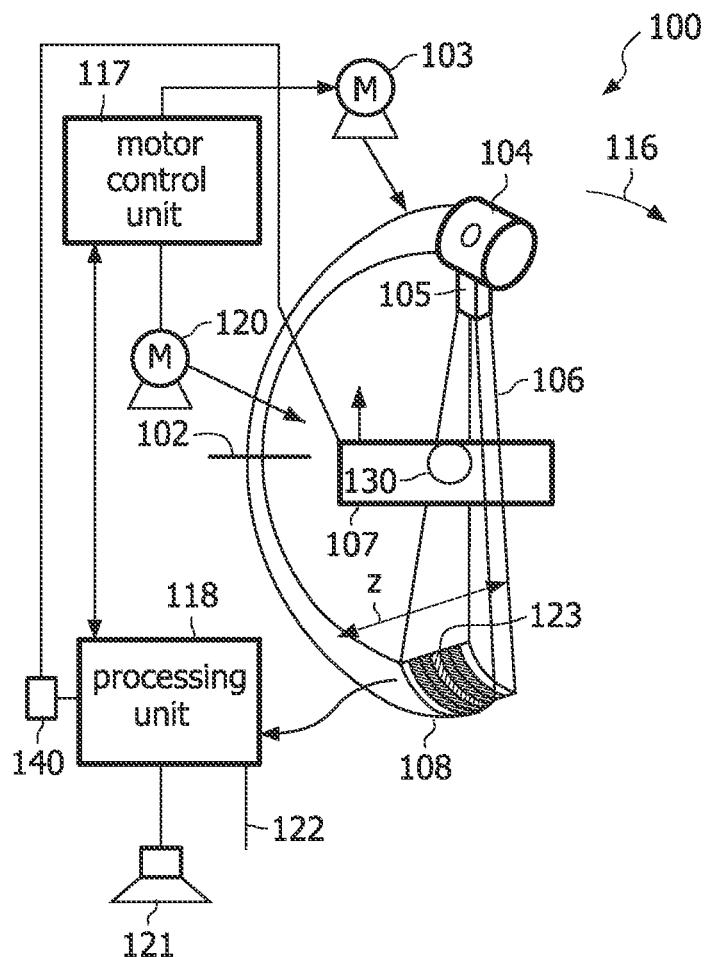
FIG. 1 shows a simplified schematic view of a CT C-arm system.

The illustration in the drawings is schematically. In different drawings, similar or identical elements are provided with similar or identical reference signs.

FIG. 1 shows a schematic representation of a schematic view of a computed tomography C-arm system according to the present invention. The computed tomography apparatus 100 depicted in FIG. 1 is a cone-beam CT C-arm system. The CT C-arm system comprises a C-arm, which is rotatable around a rotational axis 102. The C-arm is driven by means of a motor 103. Reference numeral 104 designates a X-ray tube, which emits polychromatic or monochromatic radiation.

Reference numeral 105 designates an aperture system which forms the radiation beam emitted from the radiation source 104 to a cone-shaped radiation beam 106. The cone-beam 106 is directed such that it penetrates an object of interest 107 arranged in the centre of the C-arm, i.e. in an examination region of the CT C-arm system, and impinges onto the detector 108. As may be taken from FIG. 1, the detector 108 is arranged on the C-arm opposite to the X-ray tube 104, such that the surface of the detector 108 is covered by the cone-beam 106. The detector 108 depicted in FIG. 1 comprises a plurality of detector elements 123 each capable of detecting X-rays which have been scattered by or passed through the object of interest 107.

During scanning the object of interest 107, the X-ray tube 104, the aperture system 105 and the detector 108 are rotated with the C-arm in the direction indicated by arrow 116. For rotation of the C-arm the X-ray tube 104, the aperture system 105 and the detector 108, the motor 103 is connected to a motor control unit 117, which is connected to a processing unit 118 which may comprise the synchronisation unit.

The object of interest 107 may be, for example, a patient which is disposed on an operation table not shown here. During the scan of, e.g., the head 130 of the patient 107, the C-arm rotates around the patient 107 and the focal spot moves along a circular or other trajectory (e.g. a saddle trajectory). Therefore, a scan is performed without displacement of the operation table parallel to the rotational axis 102.

The detector 108 is connected to the processing unit 118. The processing unit 118 receives the detection result, i.e. the read-outs from the detector elements 123 of the detector 108 and determines a scanning result on the basis of these read-outs. Furthermore, the processing unit 118 communicates with the motor control unit 117 in order to coordinate the movement of the C-arm with motors 103 and 120 with the operation table.

The processing unit 118 may be adapted for reconstructing an image from read-outs of the detector 108. A reconstructed image generated by the processing unit 118 may be output to a display (as shown in FIG. 1) via an interface 122.

The processing unit 118 may be realized by a computer readable medium, e.g. a data processor to process read-outs from the detector elements 123 of the detector 108.

The measured data, namely the computer tomography data are processed by the processing unit 118 which may be further controlled via a graphical user-interface 140.

Figure 2:
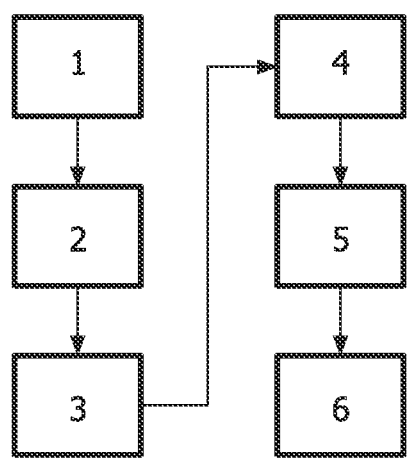
FIG. 2 shows a flow-chart of the method steps according to the present invention.

FIG. 2 shows a flow-chart of the method steps according to the present invention whereas each box represents a step of the method. The steps are:
1. Acquiring a first 3D data volume of the object using first scan parameters as shown exemplary in FIG. 4.
2. Adjusting the first data volume to a second data volume (segmented volume) such that voxel values of the first data volume of at least one predefined range of Hounsfield (H) are set to an at least one predefined H-value as shown exemplary in FIG. 6.
3. Generating a forward projection of the second data volume using the first scan parameters.
4. Reconstructing the projection to a third data volume as shown in FIG. 7.
5. Generating a fourth data volume (artefact-only volume) by subtracting the third volume with the second volume (see FIG. 8).
6. Finally, generating a fifth volume by adding the first volume with the fourth volume as shown exemplary in FIG. 9B.

Figure 3:
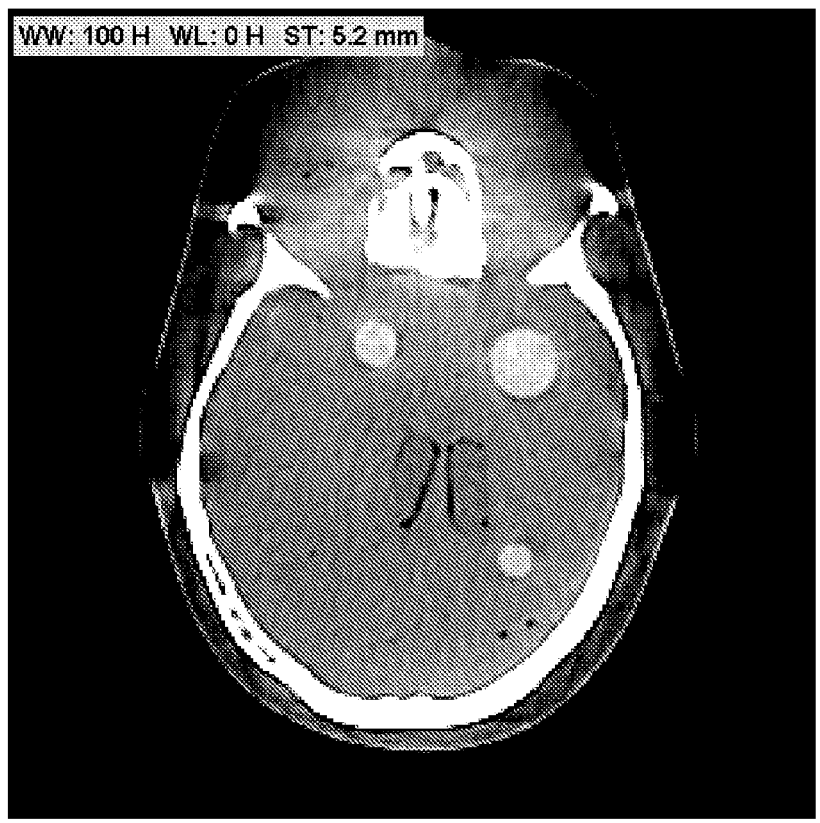
FIG. 3 shows an image of a 3D reconstruction of a head phantom, scanned with an angular range of 180° plus fan angle.

FIG. 3 shows an image of a 3D reconstruction of a head phantom, scanned with an angular range of 180° plus fan angle. The window width is 100H, window level is set to 0H as shown in the upper bar of FIG. 3. The 3D quality of the image is satisfying.

To acquire the shown image every aquired CT slice may subdivided into a matrix of N×N volume elements (voxels). Each voxel has been traversed during the scanning process by X-ray photons. The intensity of the transmitted radiation has been measured from the detector elements 123 of the detector 108 (FIG. 1). From these intensity readings, the density or attenuation value of the tissue of the object at each point in the slice can be calculated in a known way. Specific attenuation values are assigned to each individual voxel. The viewed image is then reconstructed as a corresponding matrix of picture elements (pixels). Each pixel is assigned a numerical value (CT number), which is the average of the attenuation values contained within the corresponding voxel. This number is compared to the attenuation value of water and displayed on a scale of arbitrary units named Hounsfield units or Hounsfield (H). As is generally known, this scale assigns water as an attenuation value of zero. The range of CT numbers is up to 2000 or more. Typically, bone pixels have values between +400H and +1000H. Soft tissue have values between +40H and +80H. Air have a value of −1000H.

Figure 4:
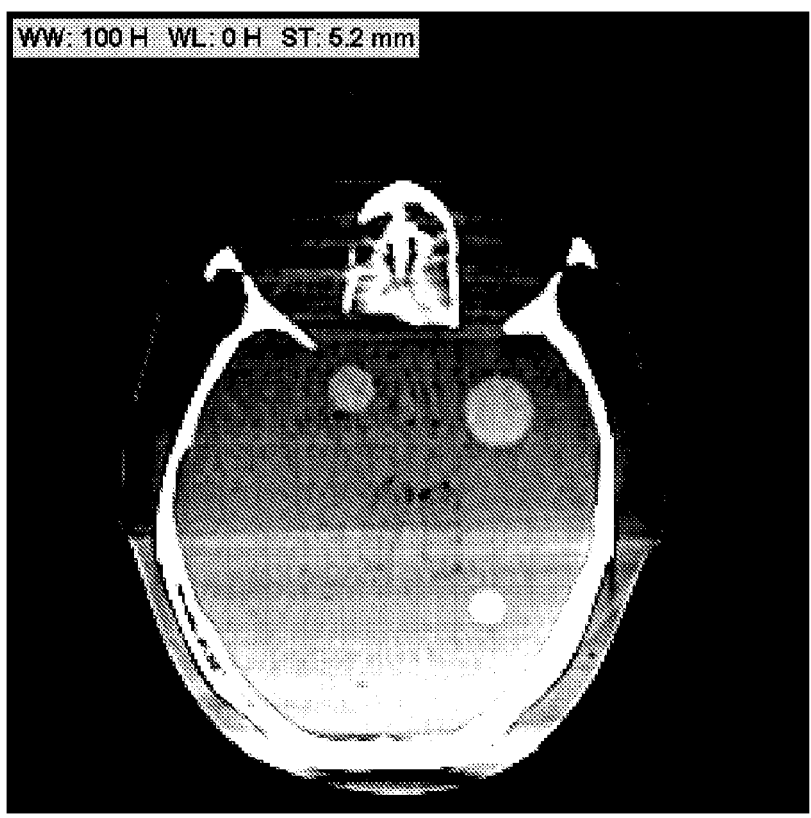
FIG. 4 shows the same phantom scanned with an angular range of 180°.

FIG. 4 shows the same skull phantom scanned with an angular range of 180°. A strong brightly vertical gradient together with horizontal streaks is obvious. This level of artefacts due to angular underscanning is unacceptable for the physician. The shown image may be called the first pass reconstruction or first pass volume.

Figure 5:
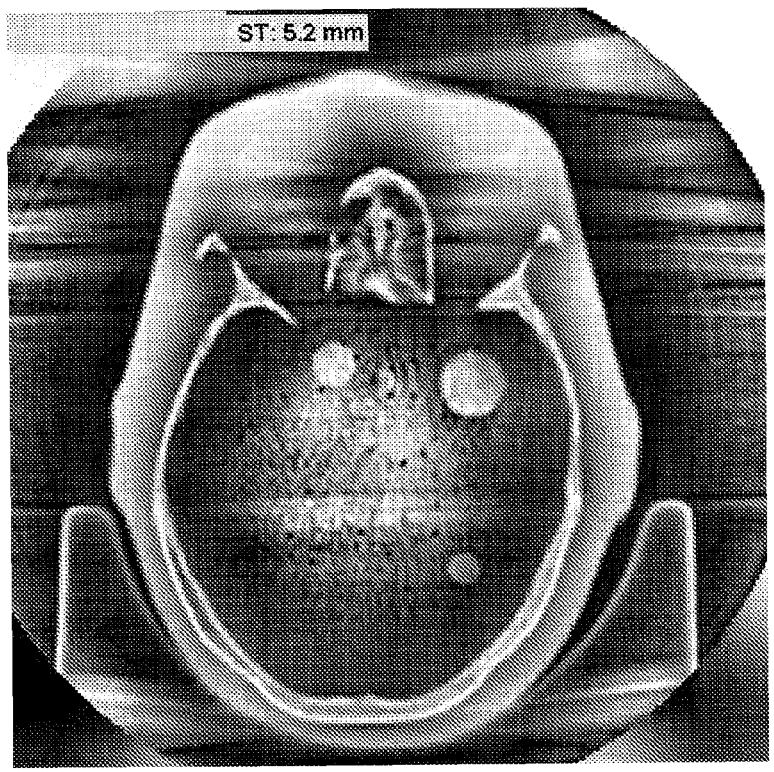
FIG. 5 shows a local-contrast enhanced version of the image of FIG. 4.

FIG. 5 shows a local-contrast enhanced version of the image of FIG. 4. It shows that streaks emanate from high-contrast boundaries. The artefacts result from the fact that different voxel received X-ray illumination over different angular ranges. Generally, when the '180°+fan angle' condition is met (as with the 180° plus fan angle image shown in FIG. 3) known algorithms as Parker Weighting described in "*Optimal short scan convolution reconstruction for fanbeam CT*", D. L. Parker, Med. Phys. 9 (2), 254-257, 1982 may be used. But when the condition is not met, strong artefacts will persist.

Figure 6:
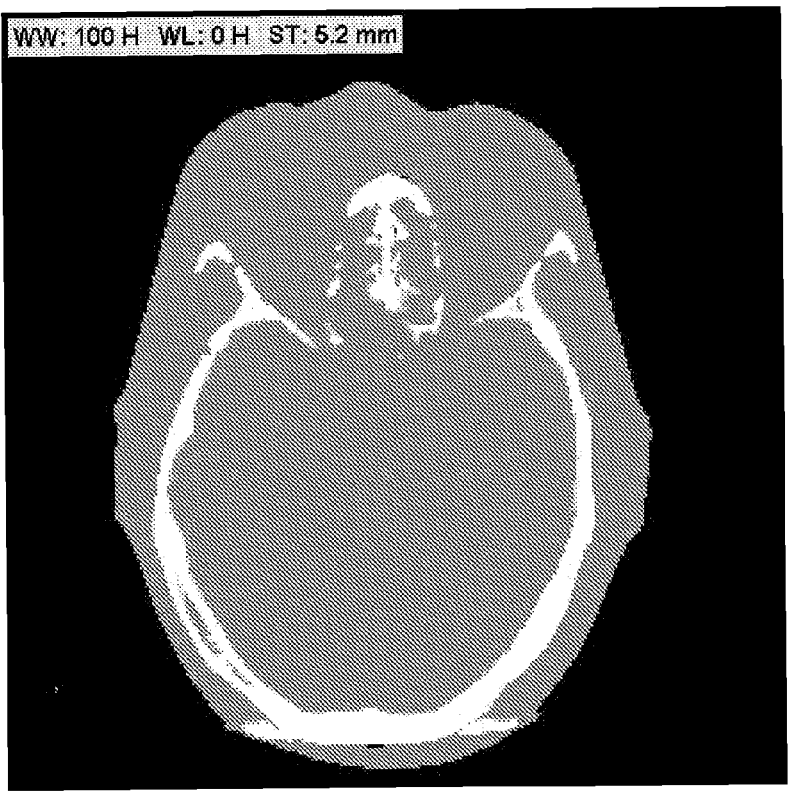
FIG. 6 shows the image of FIG. 4 with water voxels reset to 0H.
Figure 7:
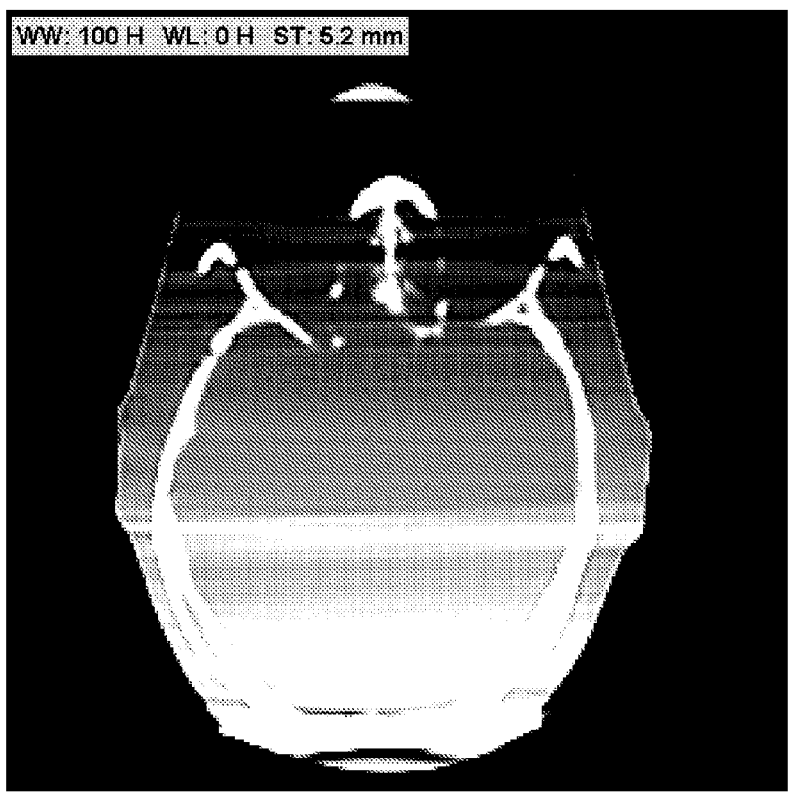
FIG. 7 shows an image acquired from a generated and reconstructed forward projection using the data volume and scan geometry parameters of FIG. 4.

FIG. 6 shows the image of FIG. 4 with water voxel, more precisely the corresponding pixel, reset to 0H and bone voxel unchanged. To correct the artefacts the image shown in FIG. 4 was segmented. Segmentation means that some or all voxel in the first data volume or first-pass volume are reset to some 'ideal' value.

FIG. 7 shows an image acquired from a generated and reconstructed forward projection using the data volume and scan geometry parameters of scan. For reconstruction a known Feldkamp algorithm may be used. Window width is again 100H and window level is set to 0H. The segmented volume, shown in FIG. 6 as the image of FIG. 7 contains sharp artificial edges. This is caused by a low-pass filtering effect occurring during the reprojection and the reconstruction. To improve the image quality in this point a similar low-pass filter may be applied to the segmented volume e.g. through single or multiple application of a simple 3×3×3 box filter before subtraction.

Figure 8:
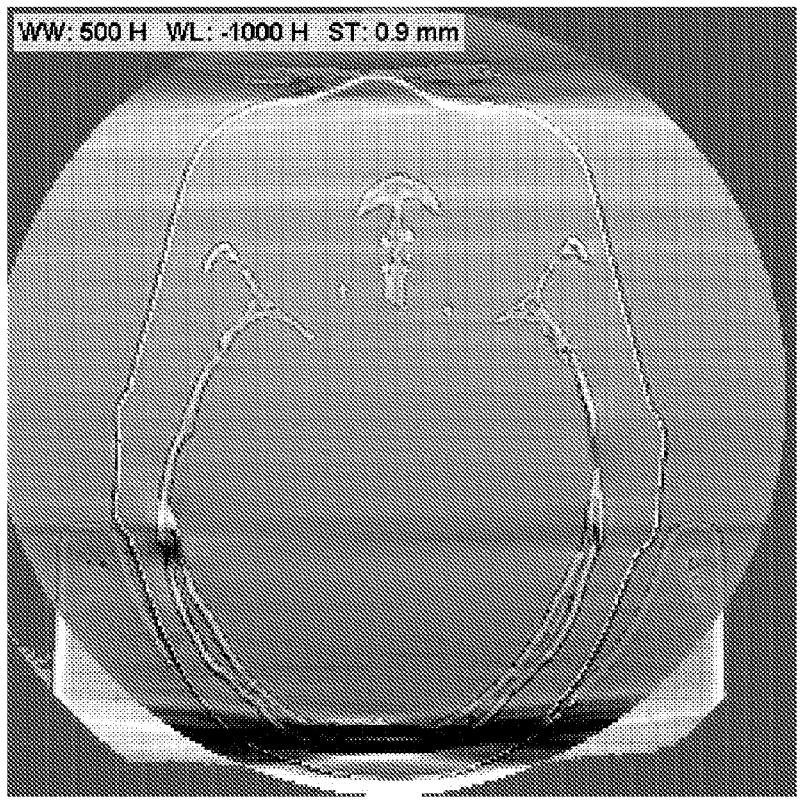
FIG. 8 shows a artefact-only image as a result of a subtraction of the image data of FIG. 7 with the image data of FIG. 4.

FIG. 8 shows a artefact-only image as a result of a subtraction of the image data of FIG. 7 with the image data of FIG. 4.

FIG. 9A shows the same image as FIG. 3 for comparing with FIG. 9B

Finally, FIG. 9B shows the artefact corrected image as a result of an addition of the image data of FIG. 9A with the image data of FIG. 8. The image quality of FIG. 9B is strongly improved compared with the image shown in FIG. 9A.

It should be noted, however, that the present invention is not limited to this specific data acquisition and reconstruction.

It should be noted that the term "comprising" does not exclude other elements or steps and the "a" or "an" does not exclude a plurality. Also elements described in association with different embodiments may be combined. It should also be noted that reference signs in the claims shall not be construed as limiting the scope of the claims.

The invention claimed is:

1. A Computer Tomography (CT) C-arm system for examination of an object of interest, the CT- C-arm system comprising:
an X-ray tube adapted for generating X-rays;
an X-ray detection unit to acquire a set of CT slices;
wherein the X-ray tube, and the X-ray detection unit are adapted to be rotatable on a C-arm around a common axis around the object under examination;
a processing unit by which the following steps are executable:
acquiring a first 3D data volume of the CT slices using first scan parameters;
adjusting the first data volume to a second data volume (segmented volume) such that voxel values of the first data volume of at least one predefined range of Hounsfield (H) are set to an at least one predefined H-value;
generating a forward projection of the second data volume using the first scan parameters;
reconstructing the projection to a third data volume;
generating a fourth data volume (artefact-only volume) by subtracting the third volume with the second volume; and
generating a fifth volume by adding the first volume with the fourth volume.

2. A method for artefact correction of a 3D data volume of Computer Tomography (CT) slices of an examined object; wherein each CT slice is scanned by a CT C-arm system at a different angle around an axis through the object in an angular range of 180° or less; wherein the method comprising the steps:
acquiring a first 3D data volume of the object using first scan parameters;
adjusting the first data volume to a second data volume (segmented volume) such that voxel values of the first data volume of at least one predefined range of Hounsfield (H) are set to an at least one predefined H-value;
generating a forward projection of the second data volume using the first scan parameters;
reconstructing the projection to a third data volume;
generating a fourth data volume (artefact-only volume) by subtracting the third volume with the second volume; and
generating a fifth volume by adding the first volume with the fourth volume.

3. The method according to claim 2; wherein the first data volume is adjusted to the second data volume such that voxel values of the first data volume of a range between −500H and 200H are set to 0H.

4. The method according to claim 3; wherein the first data volume is adjusted to the second data volume such that voxel values of the first data volume less than −850H are set to −1000H.

5. The method according to claim 2; further comprising:
reconstructing an image as a voxel corresponding matrix of picture elements (pixel) of the fifth data volume.

6. The method according to claim 2; further comprising:
applying a low-pass filter to the second data volume.

7. A computer-readable medium, in which a computer program for examination of an object of interest is stored which, when executed by a processor, causes the processor to carry out the steps of:
acquiring a first 3D data volume of CT slices using first scan parameters;
adjusting the first data volume to a second data volume (segmented volume) such that voxel values of the first data volume of at least one predefined range of Hounsfield (H) are set to an at least one predefined H-value;
generating a forward projection of the second data volume using the first scan parameters;
reconstructing the projection to a third data volume;
generating a fourth data volume (artefact-only volume) by subtracting the third volume with the second volume; and
generating a fifth volume by adding the first volume with the fourth volume.

8. A program element for examination of an object of interest, which being executed by a processor, causes the processor to carry out the steps of:
acquiring a first 3D data volume of CT slices using first scan parameters;
adjusting the first data volume to a second data volume (segmented volume) such that voxel values of the first data volume of at least one predefined range of Hounsfield (H) are set to an at least one predefined H-value;
generating a forward projection of the second data volume using the first scan parameters;
reconstructing the projection to a third data volume;
generating a fourth data volume (artefact-only volume) by subtracting the third volume with the second volume; and
generating a fifth volume by adding the first volume with the fourth volume.

* * * * *